(12) United States Patent
Maglione

(10) Patent No.: US 9,539,247 B2
(45) Date of Patent: Jan. 10, 2017

(54) NUTRACEUTICAL COMPOSITION FOR THE TREATMENT OF EXCESS WEIGHT AND MODERATE HYPERCHOLESTEROLEMIA/DYSGLYCEMIA

(71) Applicant: AKADEMY PHARMA S.r.L., Milan (IT)

(72) Inventor: Vincenzo Maglione, Monza (IT)

(73) Assignee: AKADEMY PHARMA S.r.L., Milan (IT)

( * ) Notice: Subject to any disclaimer, the term of this patent is extended or adjusted under 35 U.S.C. 154(b) by 0 days.

(21) Appl. No.: 14/950,289

(22) Filed: Nov. 24, 2015

(65) Prior Publication Data

US 2016/0151338 A1    Jun. 2, 2016

(30) Foreign Application Priority Data

Nov. 28, 2014 (IT) .............. MI2014A2050

(51) Int. Cl.

| | | |
|---|---|---|
| *A61K 31/44* | (2006.01) | |
| *A61K 31/4375* | (2006.01) | |
| *A61K 36/899* | (2006.01) | |
| *A61K 36/062* | (2006.01) | |
| *A61K 36/29* | (2006.01) | |
| *A61K 36/605* | (2006.01) | |
| *A61K 31/366* | (2006.01) | |
| *A61K 31/445* | (2006.01) | |

(52) U.S. Cl.
CPC .......... *A61K 31/4375* (2013.01); *A23L 29/035* (2016.08); *A23L 29/045* (2016.08); *A23L 33/105* (2016.08); *A61K 31/366* (2013.01); *A61K 31/445* (2013.01); *A61K 36/062* (2013.01); *A61K 36/29* (2013.01); *A61K 36/605* (2013.01); *A61K 36/899* (2013.01); *A23V 2002/00* (2013.01); *A23V 2200/328* (2013.01); *A23V 2200/3262* (2013.01); *A61K 2236/19* (2013.01)

(58) Field of Classification Search
None
See application file for complete search history.

(56) References Cited

U.S. PATENT DOCUMENTS 7,608,286 B2 * 10/2009 Olalde Rangel ....... A61K 31/44
424/725

* cited by examiner

*Primary Examiner* — Heidi Reese

(74) *Attorney, Agent, or Firm* — Vorys, Sater, Seymour & Pease LLP

(57) ABSTRACT

A nutraceutical composition is provided for the treatment of excess weight and moderate hypercholesterolemia/dysglycemia, comprising: Berberine, Monacolin K, 1-deoxynojirimycin (DNJ).

10 Claims, No Drawings

NUTRACEUTICAL COMPOSITION FOR THE TREATMENT OF EXCESS WEIGHT AND MODERATE HYPERCHOLESTEROLEMIA/DYSGLYCEMIA

FIELD OF THE INVENTION

The present invention relates to a nutraceutical composition for the treatment of excess weight and moderate hypercholesterolemia/dysglycemia.

In particular, the invention relates to a nutraceutical composition capable of reducing body weight and which can be used as a support treatment of a low-calorie diet. In addition the product contains two components able to lower cholesterol/dysglycemia in patients with excess blood cholesterol of a moderate degree.

DESCRIPTION OF THE PRIOR ART

According to the World Health Organization (WHO), overweight and obesity, in particular, are major public health problems in the world. Indeed a global epidemic is under way which is spreading in many countries and which could cause, in the absence of immediate action, very serious health problems in the coming years.

Overweight and obesity are conditions associated with premature death and are now universally recognised as risk factors for the major chronic diseases: cardiovascular disease, stroke, diabetes, some cancers (endometrial, colorectal, gallbladder, kidney and breast cancers in postmenopausal women), gallbladder disease, osteoarthritis. In addition, very often overweight patients also have an excess of fat in the blood. Among these, the most feared is the increase of cholesterol, which is associated with increased vascular risk. Hypercholesterolemia is currently treated with drugs such as statins which are very effective but which at usual dosages may be associated, at least in one case out of four, with muscular, hepatic or other side effects.

Another important problem of increasing importance in the Western world and beyond is the high probability of developing diabetes in a person of high body weight.

Lastly, with the passage of time, the rise in obesity among children and adolescents which from childhood exposes children to respiratory problems, joint problems, reduced mobility, but also to disorders of the digestive tract and psychological disorders, is becoming increasingly important.

Among the best-known techniques to help lose weight are drugs known as "diet pills" made with caffeine, ephedrine or amphetamines which increase the body's metabolism and, consequently, increase calorie consumption. These drugs, despite having important advantages, have important contraindications. The use of amphetamines may give rise to numerous ailments such as dehydration, gastrointestinal disorders, headache, hypertension, arrhythmias, angina pectoris, myocardial infarction, increased risk of stroke. Also the use of such pills makes the body develop a sort of resistance to slimming effects, thus requiring an increased dosage, with the consequent risk. Amphetamines are now banned in most Western countries. Among the most effective antiobesity drugs was sibutramine® which acts on the central nervous system using a mechanism of action similar to that of some antidepressant drugs. Sibutramine®, while giving positive results, had significant side effects which led to it being withdrawn from the market. Lastly, Orlistat®, still marketed, works by reducing the absorption of dietary fat by inhibiting gastrointestinal lipase, i.e. those enzymes which break down triglycerides into simpler fragments more easily absorbed by the intestinal mucosa (fatty acids plus monoglycerides).

Orlistat® also has significant drawbacks.

In fact, the triglycerides, having escaped the digestive process, cause the classic disorders associated with steatorrhea and, in some cases, the onset of flatulence, incontinence, oily stools, and faecal urgency.

To summarise, at present in Europe only Orlistat® is commercially available for the treatment of excess weight.

As for the treatment of hypercholesterolemia, as indicated above, statins—while highly effective drugs—can have side effects of no little significance and also it has recently been revealed that chronic treatment, especially in overweight subjects, may lead to increased risk of diabetes.

Other products for treating hypercholesterolaemia are ion exchange resins, hard to administer and with poor treatment adherence and so-called fibrates, indicated however, mainly for the treatment of hypertriglyceridemia. Interesting products are being developed, such as the monoclonal antibody antagonists of PCSK9 and the synthetic product ETC-1002, but these will in any case be drugs with specific therapeutic indications whose future availability is still under discussion. Lastly, lomitapide is a synthesis product involved in the more serious forms of hypercholesterolemia (homozygous hypercholesterolemia) of high cost and thus restricted to a limited number of patients.

SUMMARY OF THE INVENTION

In this situation the technical task underlying the present invention is to devise a nutraceutical composition for the treatment of excess weight and moderate hypercholesterolemia/dysglycemia.

Within the sphere of said technical purpose one important aim of the invention is to obtain a nutraceutical composition which is substantially free of contraindications and, therefore, usable by practically anyone.

The technical purpose and specified aims are achieved by a nutraceutical composition for the treatment of excess weight and moderate hypercholesterolemia or dysglycemia, comprising: Berberine, Monacolin K, 1-deoxynojirimycin (DNJ).

DESCRIPTION OF THE PREFERRED EMBODIMENTS

Preferred embodiments are evident from the dependent claims.

In particular, the invention relates to a nutraceutical composition or functional food or food-medication to be used for the manufacture of pills, lozenges, dilutable powders in a solvent such as water.

The nutraceutical composition according to the invention comprises a first active component, suitable to regulate the absorption of carbohydrates, resulting in decreased absorption of active substances to reduce the energy content of foods.

In particular, it permits a significant reduction of the transformation of sugars (polysaccharides) into glucose and, consequently, a slowing down of the absorption of sugars by the blood.

Such active component is an active substance defined by naturally extracted 1-Deoxynojirimycin (DNJ) preferably obtained from blackberry, from silkworm or white mulberry (*Morus Alba*). More specifically the DNJ is present in the nutraceutical component as a dry extract of *Morus Alba* leaves obtained using traditional drying methods known to the person skilled in the art and in particular starting from mulberry leaves collected at the time when they have the highest concentration of active elements (balsamic time) to ensure the maximum content of phytoactive ingredients and using ethanol and water as extraction solvents.

This active ingredient can be taken by humans at daily dosages of between 100 mg/day and 1000 mg/day, and preferably between 400 mg/day and 700 mg/day.

The nutraceutical composition preferably comprises DNJ in quantities ranging between 0.2 g and 0.5 g, and more preferably between 0.3 g and 0.4 g, which are present in about 15 g-20 g of dry extract of Morus Alba leaves.

The second active component, Berberine, is preferably present in Berberis aristata bark extract titrated to 85% in Berberine. This extract is preferably made from the bark, stem and root of barberry or Berberis Aristata using ethanol and water as extraction solvents.

This is a composition able to adjust both cholesterol levels and, to a lesser extent, blood sugar levels. It is a quaternary ammonium salt belonging to the group of benzyl-quinoline alkaloids. It is found in particular in plants of Berberis aristata, usually in the root, stem and bark. Berberine has a dual mechanism of action. On the one hand it exerts a hypoglycaemic/antidiabetic activity through insulin sensitizing by activating the enzyme AMPK (similar to the mechanism of metformin) resulting in a decreased absorption of glucose and potential weight loss. The second mechanism is instead related to the activation of hepatic receptors for LDL lipoproteins. This mechanism is exerted by very few molecules and permits a synergic activity with statins.

Berberine is present in weight in proportion to DNJ, for 1 g of DNJ, between 100 g and 150 g, and more preferably between 110 g and 130 g and more preferably still between 118 g and 122 g.

Within the composition, for every 100 g thereof, Berberine is preferably present in quantities ranging between 40 g and 50 g corresponding to 50 g-60 g of dry extract of bark of Berberis.

In addition, a third component is monacolin K or lovastatin present preferably in fermented red rice powder. So-called red rice is obtained using red rice yeast, a substance which is extracted from fermented rice.

Monacolin K is active in humans at doses between 3 and 10 mg/day, corresponding to 1-2 g of red rice powder. Monacolin K uses the classic mechanism of statins, inhibiting the HMGCoA reductase enzyme in the liver and in the main parenchyma, leading to a sharp reduction in blood cholesterol. Lastly, of particular interest with respect to statins, the monacolin K present at these concentrations in red rice powder tends to exert a reduced toxic effect on the muscles, thus leading to better patient adherence to treatment.

The monacolin K is present in weight for 1 g of DNJ, between x and y g, and more preferably between 0.5 g and 1 g, more preferably 0.7 g and 0.9 g and more preferably still between 0.8 and 0.85 g.

Within the composition, for every 100 g thereof, monacolin K is preferably present in quantities ranging between 0.1 g and 0.5 g, more preferably 0.2 g and 0.3 g corresponding to 15 g-20 g of fermented red rice powder.

In addition to these active components (DNJ, Berberine, Monacolin K) preferably there are no other active components. Bulking agents may be present such as: hydroxypropyl cellulose (silica) and sodium carboxymethyl cellulose, anti-caking agents: vegetable magnesium stearate and silicon dioxide plant and so forth.

Demonstrating the effectiveness of the nutraceutical composition comprising the three active components, namely DNJ, Berberine (B) and Red (RR) some of the studies conducted by the applicant are reported.

In detail, two experiments performed on CD-1 mice (see the monograph on FRONTIERS IN NEUROENDOCRINOLOGY, IF 2006 Nov. 4) and ob/ob mice (strain of mice homozygous for defects in the "obese" gene) divided in cages, are described. More specifically, each cage is kept at an ambient temperature of 24±2° C. with a 12 h cycle of light/dark and contains four animals belonging to one of the two types and distributed so as to have substantially equivalent body weights in the various cages.

Each group of mice was subjected, for six weeks, to a particular diet. In particular, CD-1 mice were divided into four groups fed respectively:

DN: normal diet, i.e. not enriched with fat;
HFD: high fat diet consisting of: 15 g normal rodent pellets, 10 g of roasted hazelnuts, 10 g of milk chocolate and 0.5 g of corn biscuits;
HFD+15 mg/L of DNJ, 20 mg/L of B and 6 mg/L of RR fermented and dissolved in drinking water (low dose);
HFD+30 mg/L of DNJ, 40 mg/L B and 12 mg/L of RR fermented and dissolved in drinking water (high dose).

The ob/ob mice were instead divided into three groups fed:

DN: normal diet plus feeding tube with water;
HFD: high-fat diet as indicated above;
HFD: feeding tube with 20 mg/kg of DNJ, 30 mg/kg B and 10 mg/kg of RR (low dose);
HFD and feeding tube with 40 mg/kg of DNJ, 60 mg/kg B and 20 mg/kg of RR (high dose).

Once the test period (6 weeks) was completed liver, abdominal fat (epididymal+parametrial) and blood samples were collected and analysed from CD-1 mice. The plasma and serum were in turn collected from the blood.

In particular, tables 1 and 2, below, shows the results of the CD-1 mice.

From the analysis of CD-1 mice subjected to HFD+DNJ+B+RR at low doses and high doses, a lower weight compared to those treated with HFD-only was observed respectively of 26.1 and 33% as shown in table 1. In particular, comparing various nutraceutical associations vs. HFD alone, it was found that abdominal fat, with DNJ+B+RR at low doses was significantly below that seen with HFD alone and the figure further improved at the higher dose of nutraceutical mixture. With the high dose, abdominal fat was less than twice the DN group. In addition, the liver weight increased significantly with the HFD, fell to values not far from the norm in particular at the higher dose of the three products. Lastly the hepatic enzyme data showed no alterations as a result of treatments with the two doses of nutraceutical product.

TABLE 1 analysis of biological variables in CD-1 mice (mean + SD)
°< p 0.001 vs. DN; * p < 0.001 vs. HFD and ** p < 0.0001

| CD-1 mice | DN | HFD | HFD + DNJ, B, RR low dose | HFD + DNJ, B, RR high dose |
|---|---|---|---|---|
| Initial weight (g) | 24.9 ± 2.2 | 23.9 ± 3.7 | 24.9 ± 3.8 | 24.2 ± 2.9 |

TABLE 1-continued analysis of biological variables in CD-1 mice (mean + SD)
° < p 0.001 vs. DN; * p < 0.001 vs. HFD and ** p < 0.0001

| CD-1 mice | DN | HFD | HFD + DNJ, B, RR low dose | HFD + DNJ, B, RR high dose |
|---|---|---|---|---|
| Final weight (g) | 37.5 ± 3.1 | 49.5 ± 5.1° | 45.3 ± 1.9°* | 42.7 ± 3.6°** |
| food/week | 32.9 ± 4.4 | 31.5 ± 3.7° | 28.7 ± 3.2* | 27.1 ± 4.0** |
| water week (ml) | 41.7 ± 3.2 | 44.2 ± 2.8 | 37.5 ± 3.9 | 38.0 ± 3.6 |
| Abdom fat. mg/10 g weight | 250.3 ± 38.6 | 652.7 ± 89.8°° | 537.1 ± 76.3°* | 492.3 ± 94.0°** |
| Liver weight (mg/10 g body weight) | 290.7 ± 22.5 | 451.6 ± 60.2° | 376.8 ± 56.3°* | 329.7 ± 31.8°** |
| ALT U/L | 39.3 ± 7.7 | 44.1 ± 8.3 | 45.3 ± 7.6 | 43.9 ± 6.5 |
| AST U/L | 88.5 ± 6.6 | 96.2 ± 8.3 | 102.3 ± 6.7 | 104.5 ± 8.9 |
| Alka. phosphatase. U/L | 90.3 ± 14.1 | 100 ± 14.8 | 98.3 ± 17.6 | 101.5 ± 16.4 |

TABLE 2 effects on plasma lipids, insulin, leptin and intestinal enzymes
° p < 0.01 vs. DN; p* < 0.01 vs. HFD; **p < 0.001 vs. HFD

| CD-1 mice | DN | HFD | HFD + DNJ, B, RR low dose | HFD + DNJ, B, RR high dose |
|---|---|---|---|---|
| Cholesterol mg/dl | 88.1 ± 4.8 | 215.4 ± 11.3° | 166.7 ± 12.2°°* | 144.3 ± 11.5°°** |
| TG mg/dl | 112.3 ± 6.6 | 254.1 ± 18.4°° | 200.3 ± 16.5°* | 186.4 ± 14.6°** |
| Blood sugar mg/dl | 84.0 ± 6.5 | 134.2 ± 7.8° | 106.4 ± 9.2°* | 98.3 ± 6.5** |
| Insulin pg/ml | 38.4 ± 9.1 | 95.3 ± 6.8° | 74.2 ± 8.3° | 59.3 ± 7.9°** |
| Leptin ng/ml | 0.8 ± 0.3 | 3.7 ± 0.9* | 4.0 ± 1.3°*+ | 4.1 ± 1.1° |
| Lipase U/L | 270.3 ± 39.7 | 299.0 ± 20.3° | 285.3 ± 37.5 | 282.4 ± 40.8* |

Table 2 indicating the biochemical-metabolic data, instead shows a powerful hypocholesterolemic activity of the nutraceutical both at the higher and lower dose. The triglycerides are reduced to a lesser extent, while blood sugar drops significantly, approaching the values obtained with DN, at the higher dose. There are no alterations of leptin, increased with HFD, while the value of circulating lipase remains just beyond the norm.

An examination of the lipidemic parameters thus revealed that cholesterol, triglycerides and blood sugar in CD-1 mice, fell markedly with the nutraceutical treatment (DNJ+B+RR). The insulinemia, instead, i.e. the amount of insulin in the blood, showed a marked increase with HFD and was significantly reduced with the use of nutraceuticals.

Lastly, the leptin increased dramatically with the HFD and the variations with the nutraceutical were of little significance.

After completing the analysis of CD-1 mice, we moved on to the ob/ob mice whose results are given in tables 3 and 4.

The analysis of the data obtained in ob/ob mice, as can be seen from table 3, revealed a further increase in weight with the HFD. This was reduced with the lower dose of nutraceutical and brought almost to normal with the higher dose. A reduction of the weekly food intake of about 10% was observed with the higher doses of the product in the presence of HFD. Instead no changes were detected of water intake while a modest reduction of epididymal fat and non-significant reduction of abdominal fat was achieved at the higher doses of the nutraceutical in the presence of HFD. No particular alterations of hepatic weight or enzymes were observed.

TABLE 3 analysis of biological data of ob/ob mice
° p < 0.01 vs. DN; * p < 0.01 vs. HFD; **p < 0.001 vs. HFD

| CD-1 mice | DN | HFD | HFD + DNJ, B, RR low dose | HFD + DNJ, B, RR high |
|---|---|---|---|---|
| Initial weight (g) | 42.2 ± 2.9 | 40.9 ± 3.3 | 43.0 ± 1.7 | 42.5 ± 3.4 |
| Final weight (g) | 50.2 ± 4.6 | 56.7 ± 5.9° | 54.5 ± 3.9° | 52.1 ± 4.3°** |
| Net food intake/final week | 47.2 ± 5.5 | 44.5 ± 6.1° | 43.8 ± 5.6° | 42.9 ± 4.7°* |
| Net water intake ml/week. | 38.4 ± 5.2 | 40.3 ± 6.7 | 41.1 ± 5.4 | 39.6 ± 7.1 |
| Epididymal fat mg/10 g weight | 252 ± 6.7 | 294.2 ± 10.1° | 277.3 ± 9.6° | 264.3 ± 7.9 |
| Abdomin fat. [g] | 8.6 ± 6.4 | 10.7 ± 5.1 | 9.5 ± 6.4 | 8.9 ± 7.3 |
| Liver weight (mg/10 g body weight) | 996 ± 77 | 1040 ± 88 | 977 ± 59 | 969 ± 86 |
| ALT U/L | 42.3 ± 5.1 | 44.7 ± 3.9 | 45.3 ± 4.7 | 45.9 ± 3.8 |
| AST | 66.4 ± 4.9 | 67.2 ± 5.4 | 66.9 ± 4.7 | 68.3 ± 5.8 |
| ALP | 106.3 ± 12.1 | 110.1 ± 7.8 | 108.5 ± 2.6 | 113.4 ± 10.1 |

TABLE 4

Nutraceutical effect on plasma lipids, blood glucose
and insulinemia in ob/ob mice (X ± SD) *p < 0.01 vs HFD
and DN; **p < 0.001 vs. HFD, +p < 0.01 vs. low dose

| CD-1 mice | DN | HFD | HFD + DNJ, B, RR low dose | HFD + DNJ, B, RR high dose |
|---|---|---|---|---|
| Total cholesterol mg/dl | 145.7 ± 8.3 | 181.9 ± 7.7° | 164.3 ± 5.9 | 151.2 ± 3.7** |
| TG mg/dl | 120.4 ± 6.3 | 172.1 ± 8.3° | 161.4 ± 5.2° | 144.2 ± 6.1°** |
| Blood sugar-mg/dl | 188.3 ± 11.4 | 206.2 ± 10.9° | 184.2 ± 12.9°* | 175.0 ± 9.4°** |
| Insulin pg/ml | 78.2 ± 6.5 | 88.4 ± 5.9 | 83.2 ± 4.3* | 79.3 ± 2.2 |

Table 4 shows instead how cholesterol rose markedly in the presence of HFD and decreased slightly with the low dose of nutraceutical and significantly with the higher dose. The latter brought the cholesterol values back to within the norm. The triglycerides instead changed to a lesser extent with both HFD and with the nutraceutical at the two doses. The higher dose brought the triglycerides values back to close to normal.

HFD treatment significantly increased the body weight, brought back to close to normal with the higher doses of the nutraceutical. The case of blood sugar is similar, rising slightly with the HFD and brought back to normal values at the higher doses of the nutraceutical. The behaviour of the insulinemia was analogous.

Lastly, the effect of the nutraceutical composition on glucose uptake and potentially on tolerance to carbohydrates was assessed. In fact, it seemed appropriate to assess whether the nutraceutical composition could exert a modulating activity on glucose metabolism both for the mechanism already described of stimulating the expression of insulin and hepatic metabolism, and as a direct obstacle to glucose absorption.

Wistar rats, weighing around 200 g were placed in individual metabolic cages at the temperature and light/dark conditions described above for mice. The animals were divided into two groups:
- untreated animals normal diet+saline solution by feeding tube
- animals treated with the nutraceutical mixture by daily feeding tube (40 mg/kg of DNJ, 60 mg/kg B and 20 mg/kg of RR).

The nutraceutical mixture was dissolved in about 4 ml of saline solution and administered to 10 rats in the experimental group against 4 ml of saline solution only in the control rats. The nutraceutical product or saline solution were administered daily for a period of two weeks. After two weeks the animals, after fasting for 12 hours, received sugar (1 g/kg body weight) dissolved in water, administered by a feeding tube. Glucose concentrations were terminated at the vein and the tail with ACCU-CHECK at 0, 30, 60, 90 and 120 min.

Table 5 shows the results of glycaemic variations in the control animals and in the animals treated with the nutraceutical mixture and the area under the curve determined by the trapezoid method.

It is clear that in the untreated rats there was an increase in normal blood glucose values to values of +40% compared to time 0. Pre-treatment with the nutraceutical product almost completely prevented the rise in glucose

TABLE 5 blood sugar in the two experimental groups (mg/dl) (X + SD)
$*p < 0.01; **p < 0.001$ vs. controls

| Ranges | 0 | 30' | 60' | 90' | 120' |
|---|---|---|---|---|---|
| Controls n = 10 | 73 ± 6 | 120 ± 12 | 115 ± 7 | 100 ± 5 | 78 ± 3 |
| DNJ + B + RR n = 10 | 74 ± 5 | 84 ± 6** | 82 ± 4* | 79 ± 3* | 76 ± 5 |
| AUC $t_{0\,.\,\infty}$ | | | | | |
| Controls n = 10 | 207.8 + 11.3 mg/dl/hour | | | | |
| DNJ + B − RR n = 10 | 153.1 + 8.4 mg/dl/hour | | | | |

The invention described achieves important advantages.

The advantageous combination of three nutraceutical elements makes it possible to achieve very favourable results both on body weight and lipidemic parameters.

In fact particular improvements of insulin levels emerge, both in normal mice and in ob/ob mice, with weight loss, reduction of abdominal fat content with elevated reduction of cholesterol, minor effects on triglycerides.

In particular, the study and design of a nutraceutical composition having the above three components made it possible to obtain a composition with considerable potential in reducing blood cholesterol and lipidemic parameters with a discreet effect on body weight, and lesser effect on food consumption, thereby highlighting a non-interference with the central nervous system.

In addition, as is apparent from the study of normal animals kept on a fat-rich diet and ob/ob, modest drops in insulin, not in leptin, were recorded in CD-1 mice and in ob/ob. This shows that this particular combination with DNJ, Berberine and Red Rice gives a significant metabolic result with no significant interference on the endocrine system. This result is of great significance in the treatment of hypercholesterolemia and excess weight.

In addition, the direct evaluation of the product in the rat on a classic model of glucose absorption, demonstrated a clear interference in the blood sugar rise, probably attributable to the increased tissue insulin sensitivity exercised by DNJ and probably also to a general glucose absorption barrier action. This mechanism defines the potential of the treatment both of obesity and of hyperglycemic syndromes (diabetes mellitus type 2).

In conclusion, the association of these active components is of significant interest in clinical application as support therapy to a reduced calorie diet and with possible active components, such as: high vegetable fibres, leguminous proteins or other components proven active in the treatment of hyperlipidemia and obesity.

Another advantage is given by the particular relationship between the three components, namely, 1-Deoxynojirimycin, Berberine and red rice, which, as is apparent from the above study, makes for a particularly effective action.

The ability to adjust the uptake and metabolism of fat, given by Berberine and red rice, and the ability to control body weight and glucose metabolism, given by the 1-deoxynojirimycin, makes it possible to intervene, in a particularly balanced manner, on virtually all the indices determining an increase of lipidemia and body weight and, thus, the basis of a potential increased risk of arteriosclerosis.

An additional advantage, emerging clearly during the trial, is the fact that the three nutraceutical compositions, due to the particular combination mixture ratio, does not cause substantial imbalances in diet (the consumption of food/water is not markedly altered) leading to the conclusion that it would not lead the patient to adopt an unbalanced diet.

Consequently, the nutraceutical composition is easily adaptable to any kind of diet without causing dangerous side effects.

Variations may be made to the invention described herein without departing from the scope of the inventive concept expressed in the claims.

The invention claimed is:

1. A nutraceutical composition for the treatment of excess weight and moderate hypercholesterolemia/dysglycemia, comprising:
Berberine, Monacolin K, and 1-deoxynojirimycin (DNJ).

2. The nutraceutical composition according to claim 1, wherein said Berberine is present as dry extract of the bark of *Berberis*.

3. The nutraceutical composition according to claim 1, wherein said Monacolin K is present as fermented red rice.

4. The nutraceutical composition according to claim 1, wherein said DNJ is present as dry extract of *Morus alba*.

5. The nutraceutical composition according to claim 1, in which, for each gram of DNJ, the Berberine is present in an amount of between 100 g and 150 g, by weight.

6. The nutraceutical composition according to claim 1, in which, for each gram of DNJ, the Monacolin K is present in an amount of between 0.5 g and 1 g, by weight.

7. The nutraceutical composition according to claim 1, further comprising one or more bulking agents.

8. The nutraceutical composition according to claim 1, wherein said Berberine is present in an amount of between 40 g and 50 g, per 100 g of the nutraceutical composition.

9. The nutraceutical composition according to claim 1, wherein said Monacolin K is present in an amount of between 0.1 g and 0.5 g, for each 100 g of the nutraceutical composition.

10. The nutraceutical composition according to claim 1, wherein said DNJ is present in weight, between 0.2 g and 0.5 g, for each 100 g, by weight of the nutraceutical composition.

* * * * *